United States Patent
Tirén et al.

(10) Patent No.: US 10,840,051 B2
(45) Date of Patent: Nov. 17, 2020

(54) EXTRACTION STRUCTURE FOR A UV LAMP

(71) Applicants: Lightlab Sweden AB, Uppsala (SE); Nanyang Technological University, Singapore (SG)

(72) Inventors: Jonas Tirén, Uppsala (SE); Hilmi Volkan Demir, Singapore (SG)

(73) Assignees: Lightlab Sweden AB, Uppsala (SE); Nanyang Technological University, Singapore (SG)

( * ) Notice: Subject to any disclaimer, the term of this patent is extended or adjusted under 35 U.S.C. 154(b) by 0 days.

(21) Appl. No.: 15/759,727

(22) PCT Filed: Sep. 19, 2016

(86) PCT No.: PCT/SE2016/050874
§ 371 (c)(1),
(2) Date: Mar. 13, 2018

(87) PCT Pub. No.: WO2017/052450
PCT Pub. Date: Mar. 30, 2017

(65) Prior Publication Data
US 2018/0269022 A1    Sep. 20, 2018

(30) Foreign Application Priority Data

Sep. 22, 2015  (SE) ........................................ 1551216
Oct. 8, 2015   (SE) ........................................ 1551295

(51) Int. Cl.
*H01J 5/16*       (2006.01)
*H01J 61/35*      (2006.01)
(Continued)

(52) U.S. Cl.
CPC ................. *H01J 5/16* (2013.01); *G02B 1/118* (2013.01); *H01J 61/34* (2013.01); *H01J 61/35* (2013.01);
(Continued)

(58) Field of Classification Search
CPC ........... C03C 17/006–009; G02B 1/118; H01J 61/34; H01J 61/35; H01J 61/38–48; H01J 5/16
See application file for complete search history.

(56) References Cited

U.S. PATENT DOCUMENTS 4,190,321 A * 2/1980 Dorer ...................... C23C 14/14
359/581
2006/0024018 A1  2/2006 Piehl et al.
(Continued)

FOREIGN PATENT DOCUMENTS

EP       0780880 A1    6/1997
JP    2013222925 A    10/2013
(Continued)

OTHER PUBLICATIONS

JP 2013222925 A English machine translation (Year: 2013).*
(Continued)

*Primary Examiner* — Mariceli Santiago
(74) *Attorney, Agent, or Firm* — RMCK Law Group, PLC (57) ABSTRACT

The present invention generally relates to an extraction structure for a UV lighting element. The present invention also relates to a UV lamp comprising such an extraction structure onto a substrate. The extraction structure comprises a plurality of nanostructures for anti-reflecting purposes. The nanostructures are grown on the top surface of at least one of the first and second side of the substrate.

20 Claims, 4 Drawing Sheets

(51) Int. Cl.
*H01J 61/40* (2006.01)
*G02B 1/118* (2015.01)
*H01J 61/34* (2006.01)
*H01J 61/72* (2006.01)
*H01J 65/04* (2006.01)
*H01J 61/44* (2006.01)
*H01J 63/06* (2006.01)
*A61L 9/20* (2006.01)
*A61L 2/10* (2006.01)
*B82Y 20/00* (2011.01)
*H01J 1/62* (2006.01)

(52) U.S. Cl.
CPC .............. *H01J 61/40* (2013.01); *H01J 61/44* (2013.01); *H01J 61/72* (2013.01); *H01J 63/06* (2013.01); *H01J 65/046* (2013.01); *A61L 2/10* (2013.01); *A61L 9/20* (2013.01); *B82Y 20/00* (2013.01); *H01J 1/62* (2013.01); *Y10S 977/81* (2013.01); *Y10S 977/834* (2013.01)

(56) References Cited

U.S. PATENT DOCUMENTS

| | | |
|---|---|---|
| 2010/0019261 A1 | 1/2010 | Scianna et al. |
| 2010/0149510 A1 | 6/2010 | Zaczek et al. |
| 2010/0289435 A1 | 11/2010 | Kita |
| 2011/0204489 A1 | 8/2011 | Lin et al. |
| 2012/0132618 A1 | 5/2012 | Baluja et al. |
| 2013/0170044 A1* | 7/2013 | Mont ........................ G02B 1/10 359/580 |

FOREIGN PATENT DOCUMENTS

| | | |
|---|---|---|
| WO | 2008148462 A1 | 12/2008 |
| WO | 2009006702 A1 | 1/2009 |
| WO | 2013171284 A1 | 11/2013 |
| WO | 2015143150 A1 | 9/2015 |

OTHER PUBLICATIONS

Baruah, S. et al., "Hydrothermal growth of ZnO nanostructures," Science and Technology of Advance Materials, vol. 10 (2009) 013001, 19 pages.

Kim, J. et al., "Thin film coatings that reflect virtually no light," SPIE Newsroom, May 11, 2007, 2 pages.

PCT International Search Report and Written Opinion dated Dec. 20, 2016 for PCT International Application No. PCT/SE2016/050874, 19 pages.

Sood, A. et al., "Development of Nanostructured Antireflection Coatings for EO/IR Sensor and Solar Cell Applications," Materials Sciences and Applications, 2012, vol. 3, pp. 633-639.

Xi, J. et al., "Optical thin-film materials with low refractive index for broadband elimination of Fresnel reflection," Nature Photonics, vol. 1, Nr.3, Mar. 2007, pp. 176-179.

Extended European Search Report dated May 28, 2019 for EP Application No. 16849106.6, 7 pages.

* cited by examiner

EXTRACTION STRUCTURE FOR A UV LAMP

CROSS-REFERENCE TO RELATED APPLICATIONS

This application is a 371 U.S. National Stage of International Application No. PCT/SE2016/050874, filed Sep. 19, 2016, which claims priority to Swedish Application No. 1551216-3, filed on Sep. 22, 2015 and Swedish Application No. 1551295-7, filed on Oct. 8, 2015. The disclosures of each of the above applications are incorporated herein by reference in their entirety.

TECHNICAL FIELD

The present invention generally relates to an extraction structure for a UV lighting element. The present invention also relates to a UV lamp comprising such an extraction structure.

BACKGROUND OF THE INVENTION

Ultraviolet (UV) emitting lamps are used in numerous applications. They are for example used for curing of resins (glues), for tanning, for disinfection, for fluorescence (in itself a field with many applications) and many more. These applications are wide spread. In practice, UV lamps covering a range from 180-400 nm generally uses UV light sources based on mercury (Hg) vapor, so called low pressure (LP), medium pressure (MP) and high pressure (HP) lamps, but other types are available such as for example Excimer light sources.

Light sources based on Light Emitting Diode (LED) and Field Emission Lamp (FEL) technology are emerging as alternatives. The main advantages with these technologies are that they are completely free of mercury, well known as being environmentally dangerous, and that they turn on instantly (within milliseconds) something for example LP Hg light sources tend not to do.

In forming a UV lamp, at least one of the above mentioned light sources are enclosed by an enclosing structure, the enclosing structure typically comprising a material that is transparent to UV light emitted by the UV light source. Many times, the UV lamp is also covered by an additional protective structure, again made of a material that is transparent to the desired wavelengths. A common material used, especially for wavelengths between 200 and 300 nm (in principle the UVC+UVB regions), is quartz, although a few other materials can be used as well. This wavelength range is especially interesting for germicidal (disinfecting) applications since bacteria and other organisms generally are affected in this region but not by higher wavelengths. Other applications are for example disinfection of air, sterilization of medical tools and surgery theaters, curing of resins, tanning etc.

Energy effectiveness is important for environmental reasons, lamp cost and lamp life time. For germicidal applications, the UVC energy delivered to the medium that shall be disinfected is in principle determining to what extent the living bacteria are reduced. Thus for a water purification application, the UVC wattage and the flow of the medium together, will determine to what extent the disinfections performed. In the case of a fixed volume being treated, the wattage and time will determine the same. Typical ranges in practice is to reduce the number of living organisms in the order of 1:10 000 to 1:10 000 000.

Larger disinfection systems may use several kilowatts to operate the large volume flows (usually of water). In these systems it is obvious that saving energy, i.e. improving the efficiency, becomes important. For smaller systems, such improvements may predominantly be used to lower the system cost (i.e. by using smaller lamps to reach the desired effect).

A problem facing currently available UV lamps is the light extraction efficiency of the enclosing glass structure(s) of the lamps. The light extraction efficiency of the UV lamp may be defined as the ratio between the energy of the light that has escaped outside the lamp and the energy of the light generated inside the lamp (or LED). The light extraction efficiency of the UV lamp is always less than unity (one), i.e., portions of the light generated "inside" the UV lamp never reaches the external environment.

With an urge to improve the energy efficiency of the UV lamp, there is thus is a great need to supply a solution to enhance the effectiveness for UV lamps by providing an effective light extracting technology that may be manufactured and implemented easily and cost effectively. Such a solution may help to improve performance and save energy for many UV applications.

SUMMARY OF THE INVENTION

According to an aspect of the invention, the above is at least partly alleviated by an extraction structure for a UV light source, comprising a substrate at least partly transparent to UV light, the substrate having a first and a second side, the first side of the substrate arranged to face the UV light source and to receive UV light emitted by the UV light source, and a plurality of nanostructures applied onto a top surface of at least one of the first and the second side of the substrate, the plurality of nanostructures configured to reduce an amount of UV light reflected by the substrate.

The present invention is as mentioned above, based on the understanding that to make effective lamps it is important that as much as possible of the light generated inside the light source is also coming out of the same, as the part that does not is wasted energy. By means of the invention, the efficiency of e.g. a resulting UV lamp comprising the extraction structure can be improved, using inexpensive methods. The present invention is applicable to different geometries and has been evaluated on flat quartz substrate.

A plurality of nanostructures are, as mentioned, provided on a top surface of at least one of the first and the second side of the substrate. Accordingly, these nanostructures are typically grown (or similarly formed) at the top surface, meaning that it will not be necessary to e.g. perform an etching process for achieving the desirable effect. Thus, the top surface is preferably not non-structured, but rather smooth. The top surface may thus be seen as planar, at least from a perspective of a single nanostructure (the top surface may accordingly still be e.g. curved seen from a "macro" perspective).

Preferably, the substrate is formed from a first material and the plurality of nanostructures are formed from a second material, the first material being different from the second material. Accordingly, the nanostructures are formed on top of the substrate, not formed from the substrate. The plurality of e.g. grown nanostructures are thus typically arranged as an additional layer in relation to the substrate.

For light passing through a substrate with higher refractive index $n_1$ into a medium with lower refractive index $n_2$ the light is refracted follow Snell's law:

$$n_1 \sin \theta_1 = n_2 \sin \theta_2$$

If the angle of incidence $\theta_1$ is larger than the critical angle $\theta_c$ total reflection will occur. The critical angle is given by $$\theta_c = \sin^{-1} \frac{n_2}{n_1}$$

Therefore, photons that incident on the surface with an angle larger than the critical angle, are all reflected and are either entering the lamp inwards again and may keep being reflected and are trapped inside the lamp. Secondly they may enter the glass envelope of the lamp, but will be reflected when impacting the outer glass wall and may be trapped inside the glass until they have lost the energy by e.g. absorption to the glass material. This means that in a three dimensional aspect there is a cone (commonly referred to as the light cone) in which incident light will escape.

Also for angles lower than the critical angle, portions of the incident light are still reflected. The reflectivity and the transmissivity are described by the Fresnel equations. Without going into details, the Fresnel equations describe the reflective and transmissive portions of S-polarized and P-polarized components of the electrical fields (denoting polarization perpendicular and parallel to the plane of the incident light wave, respectively).

Antireflective coatings for visible light have been known for many decades. These kinds of layers form a stepwise adoption of the refractive indices between the transparent material and its surrounding materials (air, gas, water, etc.) and in principle will act by widening the effective critical angle and reduce the amount of light that is reflected and trapped and thus increase the throughput.

In accordance to the invention, enhanced light output is achieved by using a plurality of nanostructure arranged on at least one of the first and the second side of the substrate to reduce the reflectance of light emitted by the UV light source. The nanostructures according to the invention may in some instances be referred to as e.g. nanorods, nanowires, nanotubes, nanopenciles, nanospikes, nanoneedles and nanofibres.

The nanostructures differ from the antireflective coatings in that they, in one embodiment, may also consist of separated nanostructures (thus not a continuous layer or film) and in that the nanostructures are very small, for example in the range of 5-1000 nm. These nanostructure may rely on increased scattering (e.g., via creating electromagnetic and plasmonic resonances). However, when going to such nanostructures the above classical models may not be enough, analytical models are not available and advanced computer simulations are used to study the effects. Typically such advanced models for light-extraction efficiency in the UV region use the finite-difference time-domain (FDTD) techniques to solve the Maxwell equations in the devices.

The choice of material is crucial when designing the nanostructures. In an embodiment, the nanostructures are at least partly transparent to the UV light and are selected to comprise at least one of $CaF_2$, $BaF_2$ and $SrF_2$ nanostructures. In a preferred embodiment, the plurality of nanostructures comprises $MgF_2$ nanostructures. Other possibilities are the use of $SiO_2$ nanoparticles.

In regards to the substrate, the substrate is preferably selected to be formed from at least one of borosilicate glass, soda lime glass, sapphire and quartz (e.g. including (crystalline $SiO_2$, silica, fused quartz). Other materials e.g. also the substrate being $MgF_2$ are also possible.

The exact target geometry of the nanostructures is depending on the substrate material, the medium outside the lamp and the desired wavelength that should be amplified to an optimum. The nanostructures can be placed with some variation in their geometrical properties (height, length, shape, distance). Typical dimension are 5-100 nm in width and 10-5000 nm in height.

In practice, it is desirable to be able to coat a glass sleeve, window or similar as well as lamp envelopes with the mentioned nanostructures in a way that is fast, reliable and inexpensive. In an embodiment, the plurality of nanostructures are at least partly separated from each other on at least one of the first and the second side of the substrate, for example by at least 1 nm.

However, ordered structures need a process that for example uses some kind of lithography. Lithographic methods are generally feasible but expensive and are difficult to use on curved surfaces. Thus, in an alternative embodiment the nanostructures are instead randomly arranged at least one of the first and the second side of the substrate, still giving good performance enhancements. In either case it may be desirable to arrange the nanostructures on not only one side of the substrate. Accordingly, in an embodiment the plurality of nanostructures are arranged on both sides of the substrate.

In a possible embodiment of the invention, nanostructures are formed using hydrothermal techniques. Alternatively, the nanostructures may be formed at the substrate using sputtering or any other suitable technology for the formation of the above mentioned nanostructures.

Other ways to improve light extraction such as microlenses in the glass material, lapping etc. are widely known and may be combined with the use of random UV-light extracting nanostructures.

The extraction structure according to the invention may form part of a UV lamp, further comprising a UV light source. In a possible embodiment, the UV lamp further comprises an electronic drive unit configured to operate the UV light source.

The UV light source may comprise at least one of a mercury (Hg) vapor based light source, a field emission based UV light source (FEL), a UVC Light Emitting Diode (LED), and an Excimer lamp.

It should be understood that the UV light source may comprise e.g. a plurality of LEDs and/or a combination of light sources based on different technologies to suit the application. That is, emerging technologies, such as field emission light sources (FEL) and UVC Light Emitting Diodes (LEDs), offer turn on times that are in the order of milliseconds, mainly governed by the electronic drive unit. UVC-LEDs are currently being developed, but are at this time exhibiting reportedly very short life times and very low energy efficiencies. Significant efforts are being used in order to improve this and will surely and eventually be successful. Field emission light sources may have life times in the order of 1000-6000 hours depending on the desired power density and have been measured to reach efficiencies around 10%, albeit 3-5% in the UVC region.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which:

in FIG. 1a;

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Figure 1A:
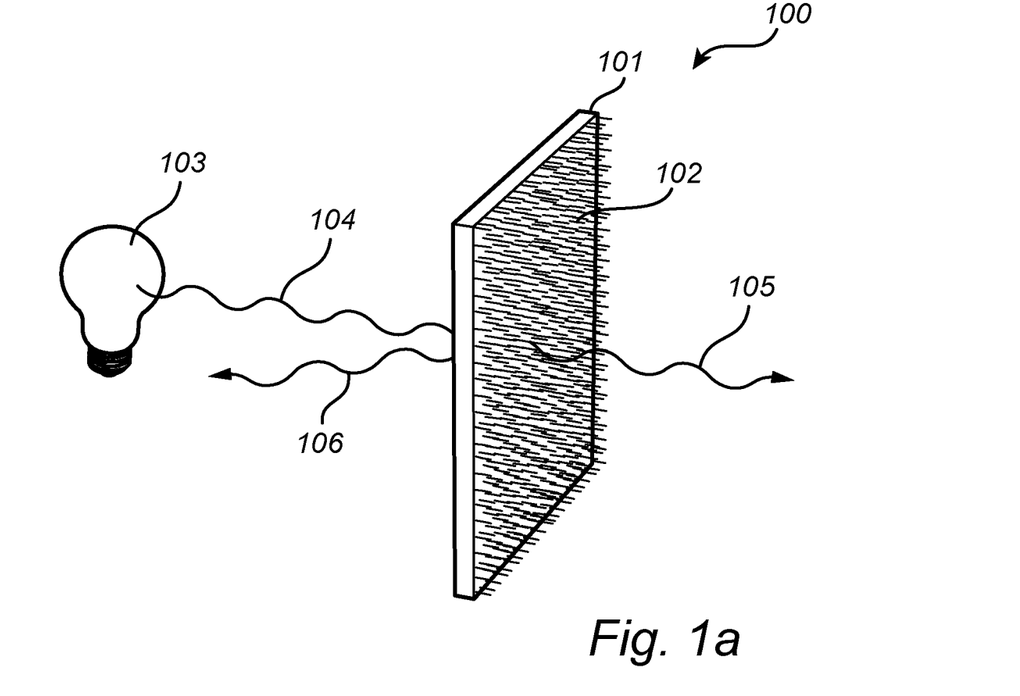
FIG. 1a disclose an exemplary extraction structure according to a currently preferred embodiment of the invention.

Referring now to the drawings and to FIG. 1a in particular, there is illustrated an extraction structure 100 comprises a flat substrate 101, which may be the envelope of a lamp or a protective cover or sleeve. A large number of randomly placed nanostructures 102 are applied to the opposite side of the omnidirectional light source 103, however they may alternatively be adopted to either one or both sides to the substrate 101. When a light beam 104 incidents on the surface of the substrate 101 it may be transmitted 105, and reflected 106 as indicated.

Figure 1B:
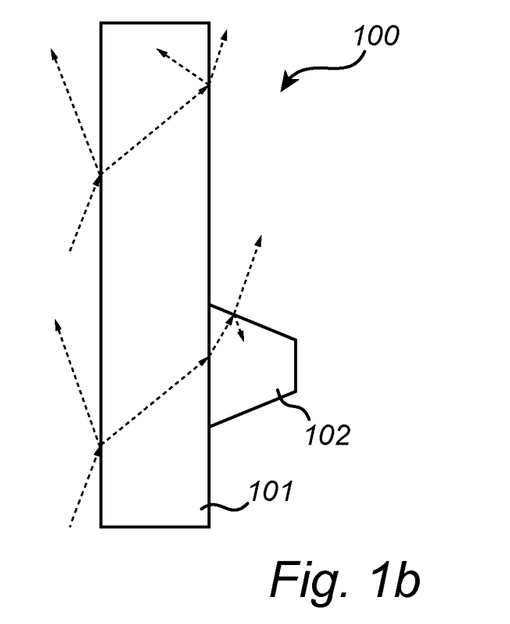
FIG. 1b shows an example of two different light paths, with and without a light extracting nanostructure, in cross section, as depicted e.g.

Using ordinary ray optics, Snell's and Fresnel's equations, is useful to understand the classical physics as part of the invention. FIG. 1b shows a cross section of the flat substrate 101 and one single randomly placed nanostructure 102. The shape of the nanostructure is drawn in an ideal manner to facilitate the understanding, and also, as understood, FIG. 1b is not to scale. On the upper section light is incident on the glass substrate with refractive index n=1.5 from air with a refractive index of n≈1. Using the mentioned equations the transmission part at this particular angle of incidence (70°, chosen arbitrarily to demonstrate the effect) is 69%—thus 31% is lost.

In the lower section the same ray optics is used, but the light will exit through the nanostructure 102. The transmission in this case is calculated to 83%. In all this is 20% higher than in the case without the nanostructure. In order to get an overall improvement this behavior must be analyzed by integration of the two cases over the angle 0-90°. It should be noted that interference, phase shifts and so forth is not taken into account here, this example is to demonstrate the usefulness. In addition nanostructures on both sides will further improve the transmission, as may the above mentioned plasmonic and electromagnetic resonance effects.

Figure 2:
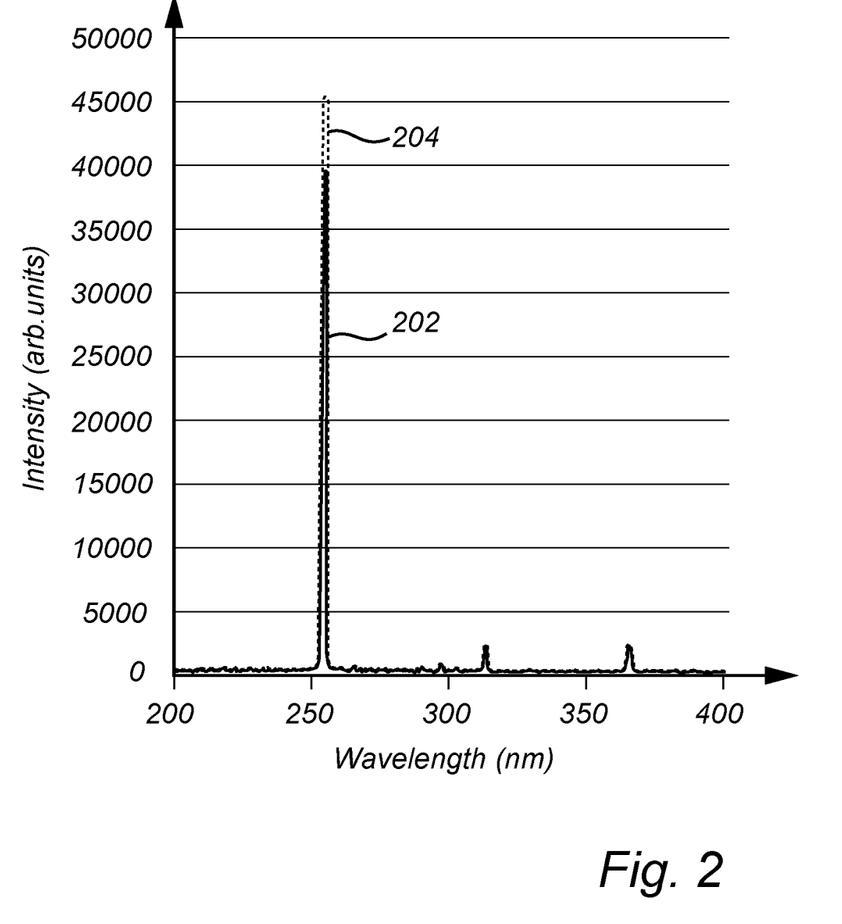
FIG. 2 is a diagram illustrating light output in the UV region with and without the inventive solution.

In FIG. 2 the measured difference in light output in the UV region, using a quartz substrate with $MgF_2$ nanostructures as indicated by FIG. 1a is shown. Line 202 indicates the case where no nanostructures are used, and line 204 where $MgF_2$ nanostructures have been applied to the substrate. As can be seen a significant improvement of around 15% at the Hg emission peak at approximately 254 nm is made.

There are several ways to implement the nanostructures. A tubular lamp envelope is used here as an example as those are commonly used but other forms are equally relevant. For example flat structures (e.g. as used in swimming pools) would be equally relevant.

Figure 3:
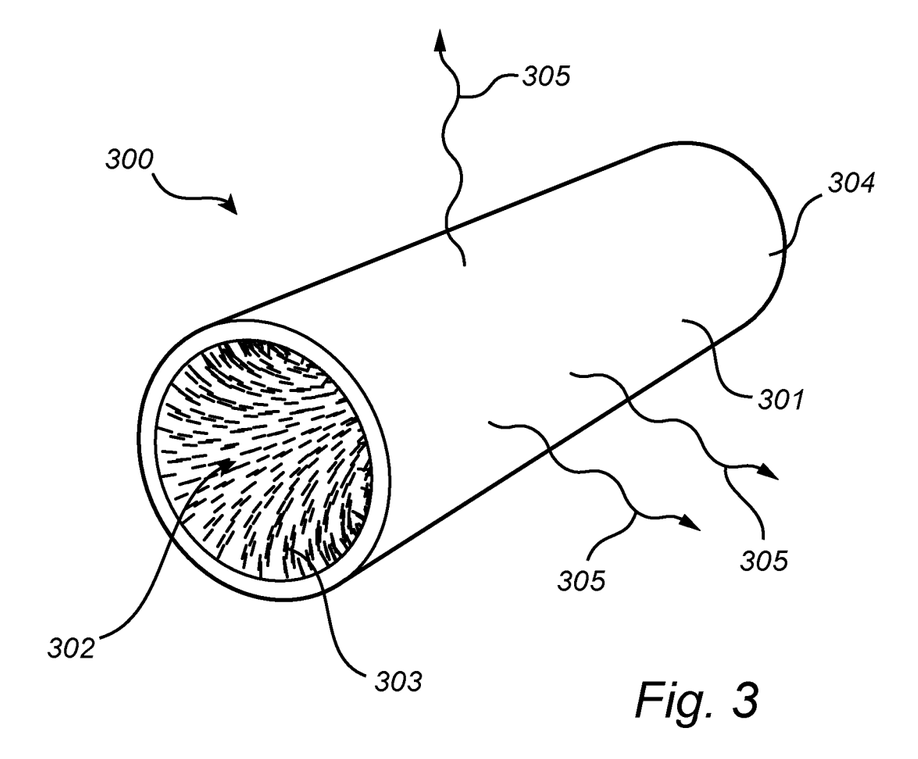
FIG. 3 shows a first exemplary embodiment of the inventive UV lamp.

In a preferred embodiment, the nanostructures are placed on the surface of the inside of a tubular lamp envelope, the envelope confining a mercury (Hg) vapor acting as the light emitting medium. Alternatively the nanostructures may be placed on the outside surface of the envelope or on both sides. This implementation is shown in FIG. 3. The first embodiment of the inventive UV lamp 300 comprises a UV transmissive envelope 301 and is filled with Hg plasma 302. Nanostructures as discussed above, e.g. $MgF_2$ nanostructures 303, 304 (the latter indicated but not shown) may be attached randomly on the inner surface or the outer surface of the envelope 301, or both. The transmission of the UV light 305 generated by the plasma 302 will thus be significantly increased.

Figure 4:
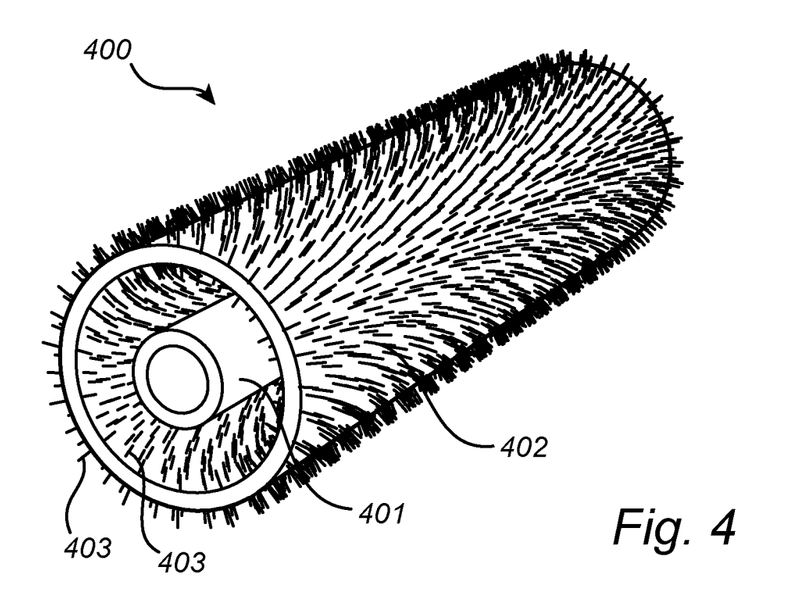
FIG. 4 shows a second exemplary embodiment of the inventive UV lamp.

Yet another embodiment of the inventive UV lamp 400 is shown in FIG. 4, comprising a mercury based UV light source 401 (which may or may not contain nanostructures as described in the second preferred embodiment above) is protected by a sleeve 402, typically by quartz, which protects the surrounding media (water, air, etc.) should the lamp break, e.g. to prevent Hg to enter the surrounding media. In this case it is possible to place light extracting features, nanostructures 403, on the inside surface or the outside surface of the protective sleeve, or both surfaces, depending on what the application requires.

Figure 5:
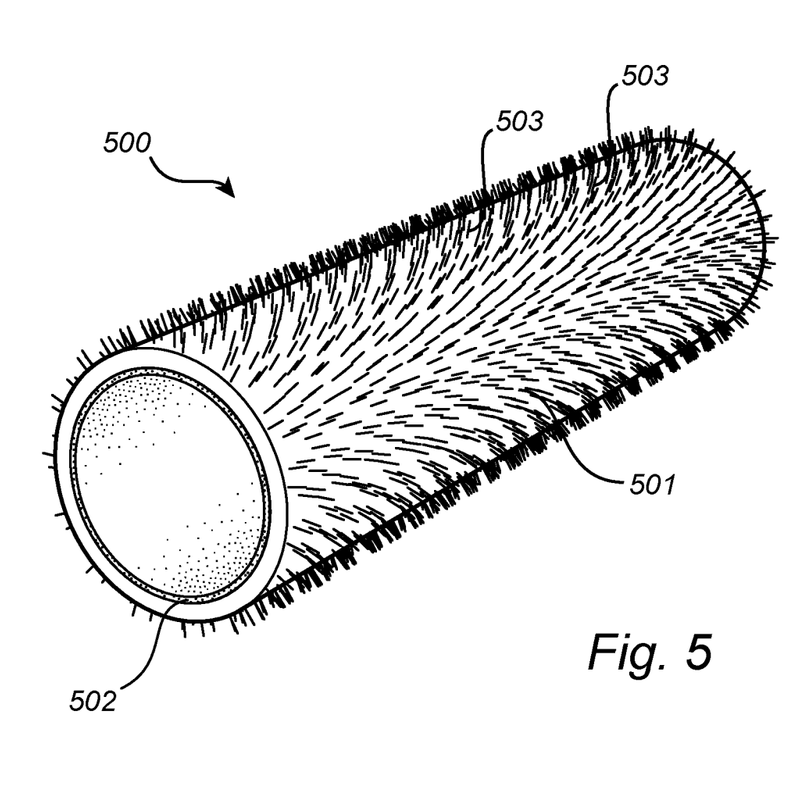
FIG. 5 shows a third exemplary embodiment of the inventive UV lamp.

In yet another implementation, as is shown in FIG. 5, the light is generated in a light powder, either by electron bombardment such as used in Field Emission Lamps or by a lower wavelength mercury plasma or in other ways (e.g. Excimer lamps. The lamp 500 consists of an envelope 501 which is covered on the inside of a light generating material 502 usually referred to as a "phosphor" or a "light powder". Since this light generating material 502 in general has a higher refractive index as compared to the light extracting materials mentioned above, it is not advantageous to place the nanostructures between the light generating layer 502 and the lamp envelope 501. In this case the nanostructures 503 are advantageously placed on the outside of the lamp envelope as previously discussed. Obviously the nanostructures 503 may be adapted to the surfaces of any transparent cover to UV lamps in order to increase the UV output of such an arrangement.

In case of using a FEL light source, the FEL light source will comprise a (centrally arranged, not shown) field emission cathode and an electrically conductive anode structure, where the anode structure for example may be arranged adjacently to the light generating material 502. During operation, a power supply will be configured to apply a high voltage between the cathode and the anode such that electrons will be emitted from the cathode towards the anode. Once the electrons are received by the adjacently arranged light generating material 502, the light generating material 502 will emit photos, i.e. UV light.

The nanostructures may be deposited in several ways. Hydrothermal techniques have been tested followed by a heat treatment. The shape of the nanostructures may be rectangular pillars, slanted pillars, spherical segments etc.

Several of the possible methods to deposit such layers are by nature random, and all the resulting nanostructures will not have the exact same dimensions but will be characterized by distribution. Their average width is typical ranging from 5-500 nm and their average heights from 5-1500 nm. The exact desired shape and dimension is e.g. determined by the exact wavelength distribution to be transmitted, the exact refractive indices of other materials involved as well as the refractive index of the media surround the light source. The nanostructures should in general be separated from each other but may also form a continuous layer closest to the surface of the substrate or envelope surface. The average separation of the nanostructures should be in the range of 0.1-1000 nm. It should be noted that, since the nanostructures are randomly placed, it is inevitable that some nanostructures will be attached to each other (i.e. not separated). Furthermore, the nanostructures may themselves be composed by even smaller substructures.

Sputtering may be an alternative approach as well as mechanical (spray, slurry, sedimentation, sol-gel) techniques, followed by heat treatment schemes to ensure adhesion and an optical interface. Other methods are equally possible and within scope of the invention In summary, the present invention relates to an extraction structure for a UV light source, comprising a substrate at least partly transparent to UV light, the substrate having a first and a second side, the first side of the substrate arranged to face the UV light source and to receive UV light emitted by the UV light source, and a plurality of nanostructures arranged on at least one of the first and the second side of the substrate, the plurality of nanostructures configured to reduce an amount of UV light reflected by the substrate.

By means of the invention, the efficiency of e.g. a resulting UV lamp comprising the extraction structure can be improved, using inexpensive methods.

Although the figures may show a specific order of method steps, the order of the steps may differ from what is depicted. Also two or more steps may be performed concurrently or with partial concurrence. Additionally, even though the invention has been described with reference to specific exemplifying embodiments thereof, many different alterations, modifications and the like will become apparent for those skilled in the art. For example, it should be mentioned that light extraction in the visible region (400-800 nm) is also improved.

Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

The invention claimed is:

1. An extraction structure for a UV light source, comprising:
 a substrate at least partly transparent to UV light, the substrate having a first and a second side, the first side of the substrate arranged to face the UV light source and to receive UV light emitted by the UV light source; and
 a plurality of nanostructures applied onto a top surface of at least one of the first and the second side of the substrate, the plurality of nanostructures configured to reduce an amount of UV light reflected by the substrate,
 wherein the nanostructures are separated from each other on at least one of the first and the second side of the substrate,
 wherein an average separation between the nanostructures is in a range of 0.1 to 1000 nm, and
 wherein the width of the plurality of nanostructures is between 5-500 nm and the length of the nanostructures is between 5-1500 nm.

2. The extraction structure according to claim 1, wherein the plurality of nanostructures are grown on the top surface of the at least one of the first and the second side of the substrate.

3. The extraction structure according to claim 1, wherein the top surface is non-structured.

4. The extraction structure according to claim 1, wherein the top surface is smooth.

5. The extraction structure according to claim 1, wherein the top surface is planar.

6. The extraction structure according to claim 5, wherein the top surface is planar as seen from a perspective of a single nanostructure.

7. The extraction structure according to claim 1, wherein the substrate is formed from a first material and the plurality of nanostructures are formed from a second material, the first material being different from the second material.

8. The extraction structure according to claim 1, wherein the plurality of nanostructures are formed at the top surface of the least one of the first and the second side of the substrate as an additional layer in relation to the substrate.

9. The extraction structure according to claim 1, wherein the plurality of nanostructures are at least partly transparent to the UV light.

10. The extraction structure according to claim 1, wherein the plurality of nanostructures comprises at least one of $CaF_2$, $BaF_2$ and $SrF_2$ nanostructures.

11. The extraction structure according to claim 1, wherein the plurality of nanostructures comprises $MgF_2$ nanostructures.

12. The extraction structure according to claim 1, wherein the substrate comprises at least one of borosilicate glass, soda lime glass, sapphire MgF2, and quartz.

13. The extraction structure according to claim 1, wherein the plurality of nanostructures are applied using hydrothermal techniques.

14. A UV lamp, comprising:
 a UV light source, and
 an extraction structure according to claim 1.

15. The UV lamp according to claim 14, wherein the extraction structure is arranged as an envelope of the UV light source.

16. The UV lamp according to claim 14, wherein UV light source comprises at least one of a mercury (Hg) vapor based light source, a field emission based UV light source (FEL), a UVC Light Emitting Diode (LED), and an Excimer lamp.

17. The UV lamp according to claim 14, wherein the first side of the substrate is provided with a light generating material and the plurality of nanostructures are applied onto the top surface of the second side of the substrate.

18. An extraction structure for a UV light source, comprising:
 a substrate at least partly transparent to UV light, the substrate having a first and a second side, the first side of the substrate arranged to face the UV light source and to receive UV light emitted by the UV light source; and
 a plurality of nanostructures applied onto a top surface of each of the first and the second side of the substrate, the plurality of nanostructures configured to reduce an amount of UV light reflected by the substrate, wherein the nanostructures are at bast partly separated from each other.

19. The extraction structure according to claim 18, wherein an average separation between the nanostructures is in a range of 0.1 to 1000 nm.

20. The extraction structure according to claim 19, wherein the width of the plurality of nanostructures is between 5-500 nm and the length of the nanostructures is between 5-1500 nm.

* * * * *